(12) United States Patent
Napholz (10) Patent No.: US 7,841,999 B2
(45) Date of Patent: Nov. 30, 2010

(54) ADJUSTABLE HINGE FOR ORTHOPEDIC BRACE

(75) Inventor: Michael Napholz, Newton, NJ (US)

(73) Assignee: EBI, LLC, Parsippany, NJ (US)

( * ) Notice: Subject to any disclaimer, the term of this patent is extended or adjusted under 35 U.S.C. 154(b) by 246 days.

(21) Appl. No.: 12/197,365

(22) Filed: Aug. 25, 2008

(65) Prior Publication Data

US 2010/0049108 A1 Feb. 25, 2010

(51) Int. Cl.
*A61F 5/00* (2006.01)
(52) U.S. Cl. .................................................. 602/16
(58) Field of Classification Search ............. 602/16, 602/20–22, 23–27; 128/882
See application file for complete search history.

(56) References Cited

U.S. PATENT DOCUMENTS

| | | | |
|---|---|---|---|
| 4,337,764 A | 7/1982 | Lerman | |
| 4,554,913 A | 11/1985 | Womack et al. | |
| 4,697,583 A | 10/1987 | Mason et al. | |
| 4,777,941 A | 10/1988 | Borig et al. | |
| 4,817,588 A | 4/1989 | Bledsoe | |
| 4,886,054 A | 12/1989 | Castillo et al. | |
| 4,915,098 A | 4/1990 | Young et al. | |
| 5,000,170 A | 3/1991 | Young et al. | |
| 5,292,303 A | 3/1994 | Bastyr et al. | |
| 5,376,134 A | 12/1994 | Biedermann et al. | |
| 5,672,152 A | 9/1997 | Mason et al. | |
| 5,814,000 A | 9/1998 | Kilbey | |
| 5,817,040 A | 10/1998 | Hess et al. | |
| 5,938,629 A | 8/1999 | Bloedau | |
| 5,997,493 A | 12/1999 | Young et al. | |
| 6,039,709 A * | 3/2000 | Bzoch ......................... | 602/26 |
| 6,129,690 A | 10/2000 | Hamlin et al. | |
| 6,375,632 B1 | 4/2002 | Albrecht et al. | |
| 6,656,144 B1 | 12/2003 | Coligado | |
| 7,037,287 B2 | 5/2006 | Cormier et al. | |
| 7,201,728 B2 | 4/2007 | Sterling | |
| 7,235,059 B2 | 6/2007 | Mason et al. | |
| 7,517,330 B2 * | 4/2009 | Deharde et al. ............... | 602/16 |
| 2006/0009722 A1 * | 1/2006 | Seligman ..................... | 602/16 |

* cited by examiner

*Primary Examiner*—Michael A. Brown
(74) *Attorney, Agent, or Firm*—Harness, Dickey (57) ABSTRACT

An adjustable hinge for an orthopedic brace includes a housing, first and second members and first and second control devices rotatably supported by the housing. The first member has a first gear portion pivotable about a first axis, and first and second cam surfaces. The second member has a second gear portion pivotable about a second axis and engageable with the first gear portion. The second axis is parallel and spaced apart from the first axis. The first control device has a third cam surface that is selectively rotatable in and out of engagement with the first cam surface and controlling a range of motion in a first rotational direction. The second control device has a fourth cam surface that is selectively rotatable in and out of engagement with the second cam surface and controlling a range of motion in a second rotational direction opposite to the first rotational direction.

20 Claims, 10 Drawing Sheets

ADJUSTABLE HINGE FOR ORTHOPEDIC BRACE

Various known orthopedic braces for the knee or elbow include devices for adjusting the range of motion of the joint. Some of these devices use removable stops or have large hinges operable by pressing buttons or moving sliders.

The present teachings provide a compact adjustable hinge for a brace that can also be used for pediatric applications.

SUMMARY

The present teachings provide a medical device that includes an adjustable hinge for an orthopedic brace. The adjustable hinge includes a housing, and first and second members rotatably supported by the housing. The first member has a first gear portion pivotable about a first axis, a first plurality of teeth, and first and second cam surfaces. The second member has a second gear portion pivotable about a second axis, and a second plurality of teeth engageable with the first plurality of teeth. The second axis is parallel and spaced apart from the first axis. The adjustable hinge also includes first and second control devices rotatably supported by the housing. The first control device has a third cam surface, the third cam surface selectively rotatable in and out of engagement with the first cam surface of the first gear portion and controlling a range of motion of the first and second gear portions in a first rotational direction. The second control device has a fourth cam surface, the fourth cam surface selectively rotatable in and out of engagement with the second cam surface of the first gear portion and controlling a range of motion of the first and second gear portions in a second rotational direction opposite to the first rotational direction.

In another aspect, the present teachings provide a medical device including an orthopedic brace for an anatomic joint, an adjustable hinge coupled to the brace and controlling a range of motion of the anatomic joint, and first and second brace arms connected to the orthopedic brace at opposite sides to the anatomic joint. The adjustable hinge includes first and second gear portions rotatable about first and second axes, and coupled to the first and second brace arms. The first and second axes are parallel to and spaced apart from one another, and also perpendicular to the first and second gear portions. The first gear portion includes a first cam surface. The adjustable hinge also includes a flexion control device having a flexion cam surface. The flexion control device is selectively rotatable about a third axis parallel to the first and second axes. The flexion cam surface engages the first cam surface of the first gear portion at a selected angle of flexion of the anatomic joint and prevents further flexion.

The present teachings further provide a method of controlling a range of motion of an anatomic joint. The method includes attaching a first brace portion to a first anatomic member of the joint, attaching a second brace portion to a second anatomic member of the joint, connecting the first brace portion to a first brace arm, and connecting the second brace portion to a second brace arm. The method further includes coupling the first brace arm to an adjustable hinge for rotation about a first pivot axis of the adjustable hinge, and coupling the second brace arm to the adjustable hinge for rotation about a second pivot axis of the adjustable hinge, the second pivot axis parallel to the first pivot axis. The method also includes rotating a flexion control device of the adjustable hinge about a third pivot axis parallel to the first and second pivot axes by a first selected degree of rotation, and limiting a range of flexion between the first and second brace arms based on the selected degree of rotation.

Further areas of applicability of the present teachings will become apparent from the description provided hereinafter. It should be understood that the description and the specific examples illustrated are intended for purposes of illustration only and are not intended to limit the scope of the present teachings.

BRIEF DESCRIPTION OF THE DRAWINGS

The present teachings will become more fully understood from the detailed description and the accompanying drawings, wherein.

DESCRIPTION OF VARIOUS ASPECTS

The following description is merely exemplary in nature and is in no way intended to limit the present teachings, applications, or uses. For example, although the present teachings are illustrated for leg braces, the present teachings can be used for elbow or other braces in both adult and pediatric applications.

Figure 1:
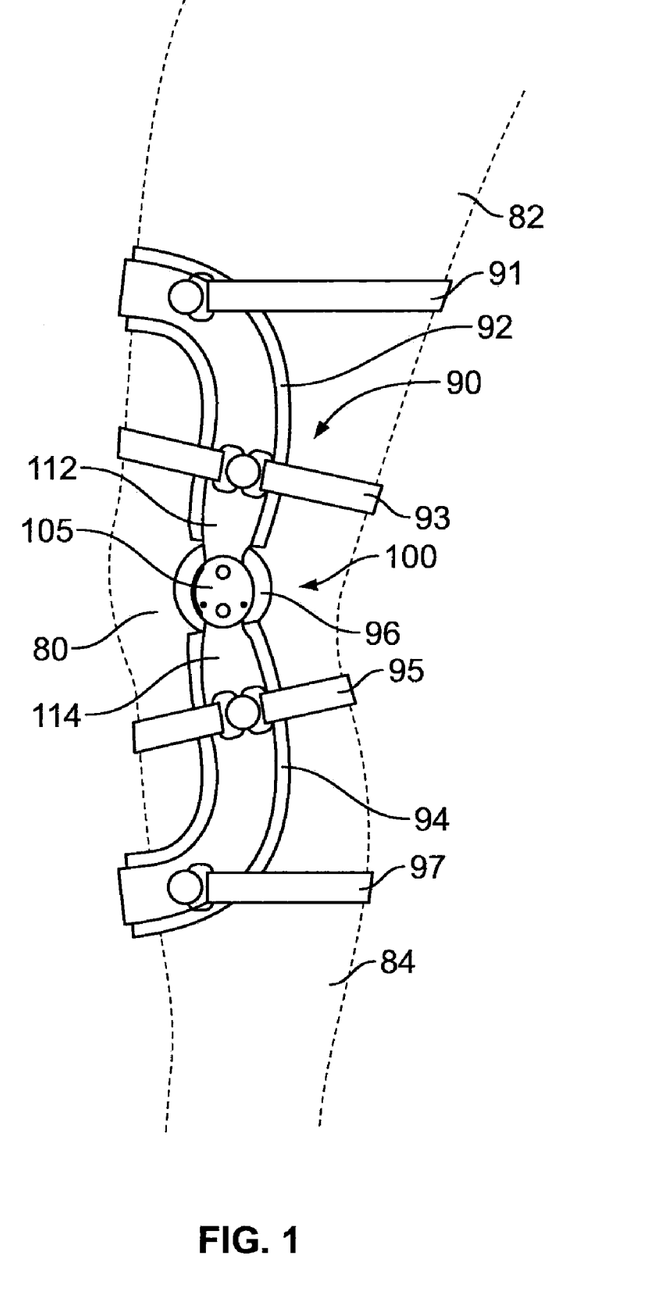
FIG. 1 is an environmental view of an adjustable hinge according to the present teachings, the adjustable hinge shown with an orthopedic brace.

Referring to FIG. 1, an adjustable hinge 100 according to the present teachings is illustrated with an orthopedic brace 90. The adjustable hinge 100 can be used with any brace 90 that permits a range of motion for an anatomic joint 80 between two bones 82, 84, such as a knee brace or an elbow brace. The adjustable hinge 100 can be sized for adult or pediatric applications while retaining control of the entire range of motion of the joint for each application. The adjustable hinge 100 can be compact in size and can allow the patient, physician or other healthcare professional to have an unlimited amount of adjustment in the range of motion for a knee or elbow brace 90.

Referring to FIGS. 2A-10, the adjustable hinge 100 can include a housing 105 having a front cover 102 with a front outer surface 102a and a back cover 104 with a back outer surface 104a. The housing 105 can support first and second members 109, 111 for pivotable motion about respective first and second axes A, B. The first and second axes A, B can be parallel and spaced apart relative to one another. The first and second axes A, B can perpendicular to a plane defined by the plate-like housing 105. The first and second axes A, B can be centered in corresponding rivets or other pivot members 106 which pass through the housing 105 and through corresponding openings 147 of the first and second members 109, 111. The pivot members 106 can be fastened or otherwise attached to a supporting pad 96 or a portion of the orthopedic brace 90. It will be appreciated that the housing 105 is merely exemplary, and a housing 105 of different shape and size can also be used depending on the application and/or the orthopedic brace 90.

Figure 4:
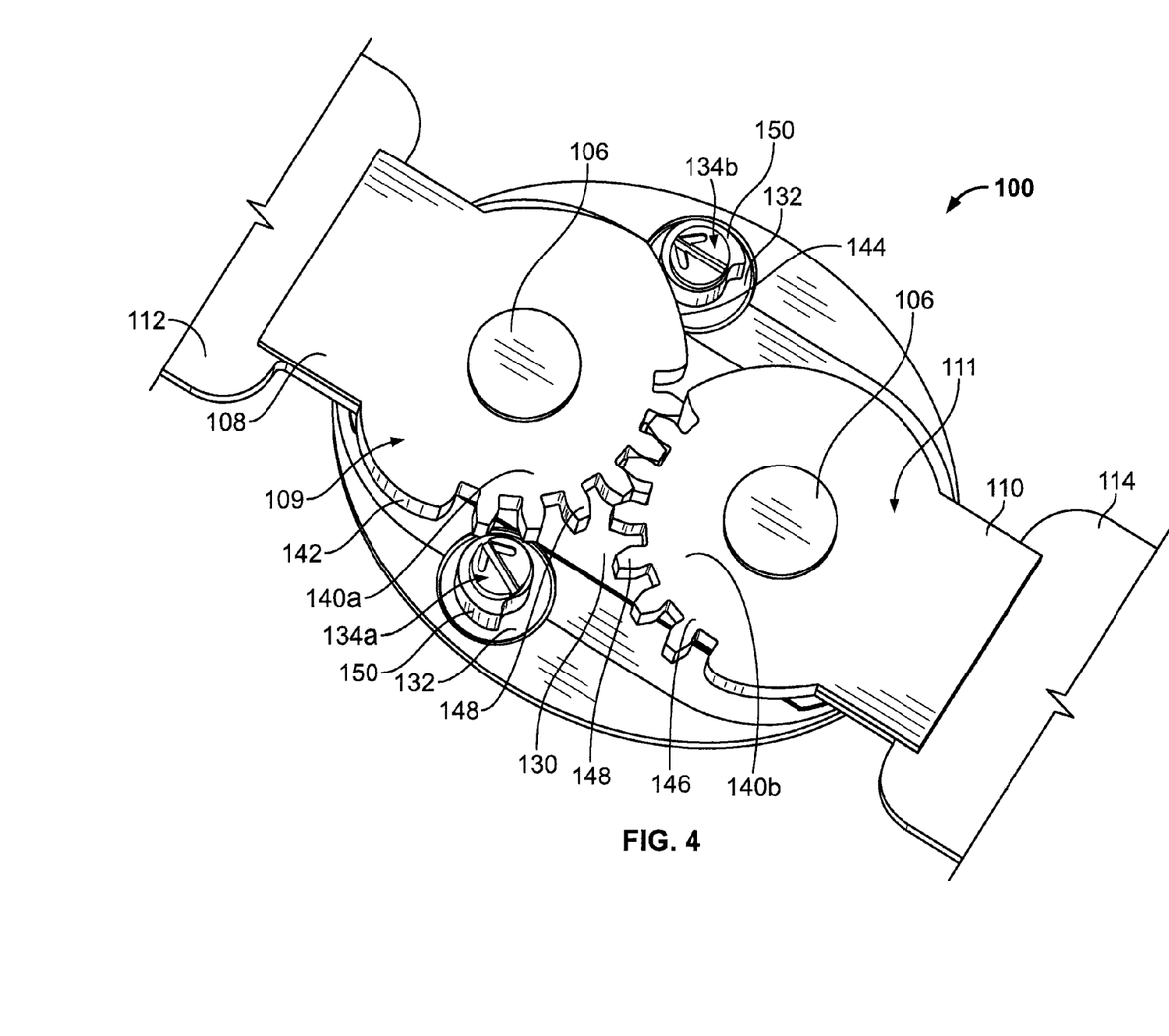
FIG. 4 is a perspective view of the adjustable hinge of FIG. 2A, shown with a front cover removed.
Figure 5:
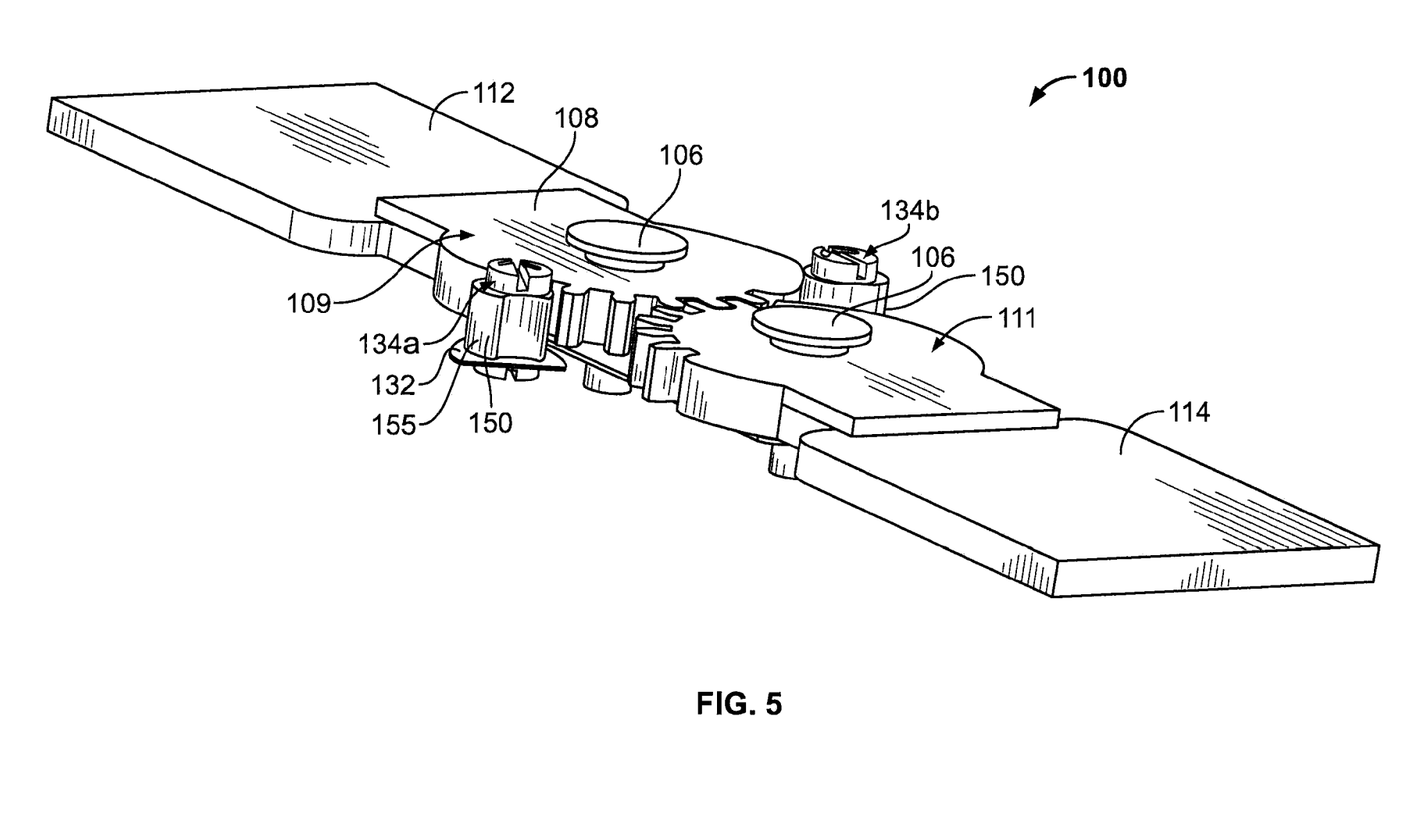
FIG. 5 is a perspective view of the adjustable hinge of FIG. 2A, shown with back and front covers removed.
Figure 6:
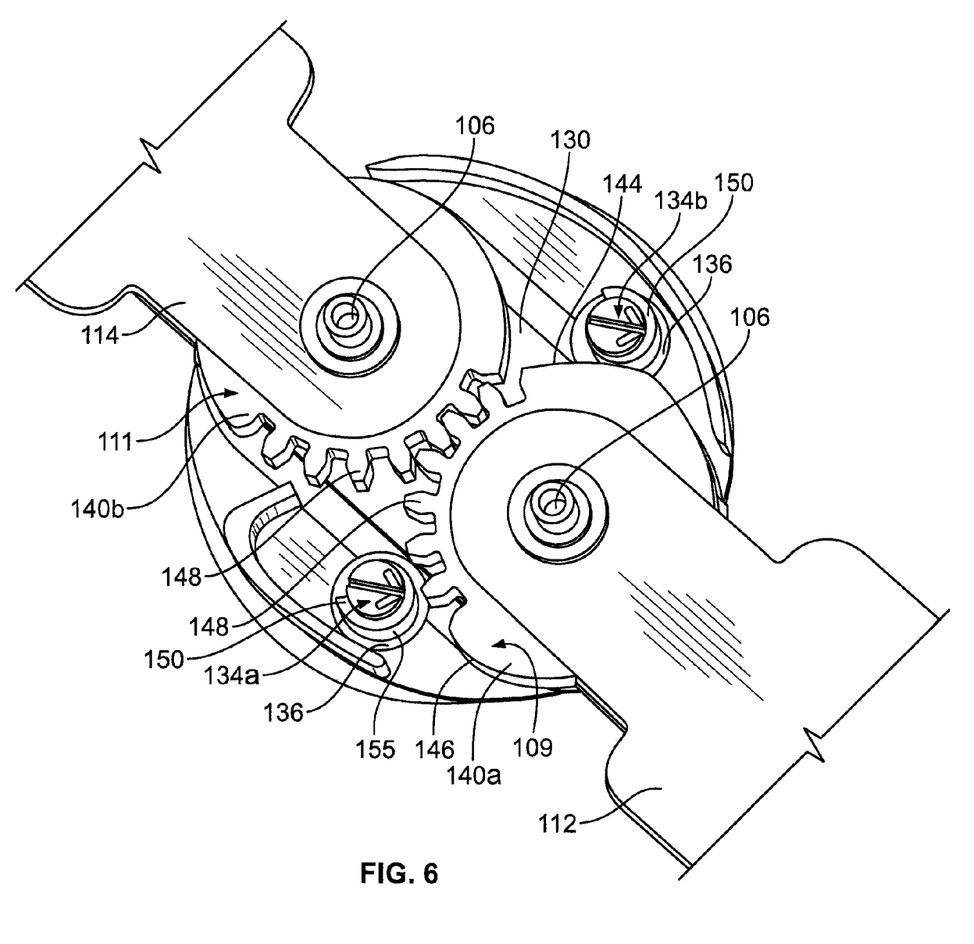
FIG. 6 is a perspective view of the adjustable hinge of FIG. 2A, shown with first and second brace arms in extension.
Figure 7:
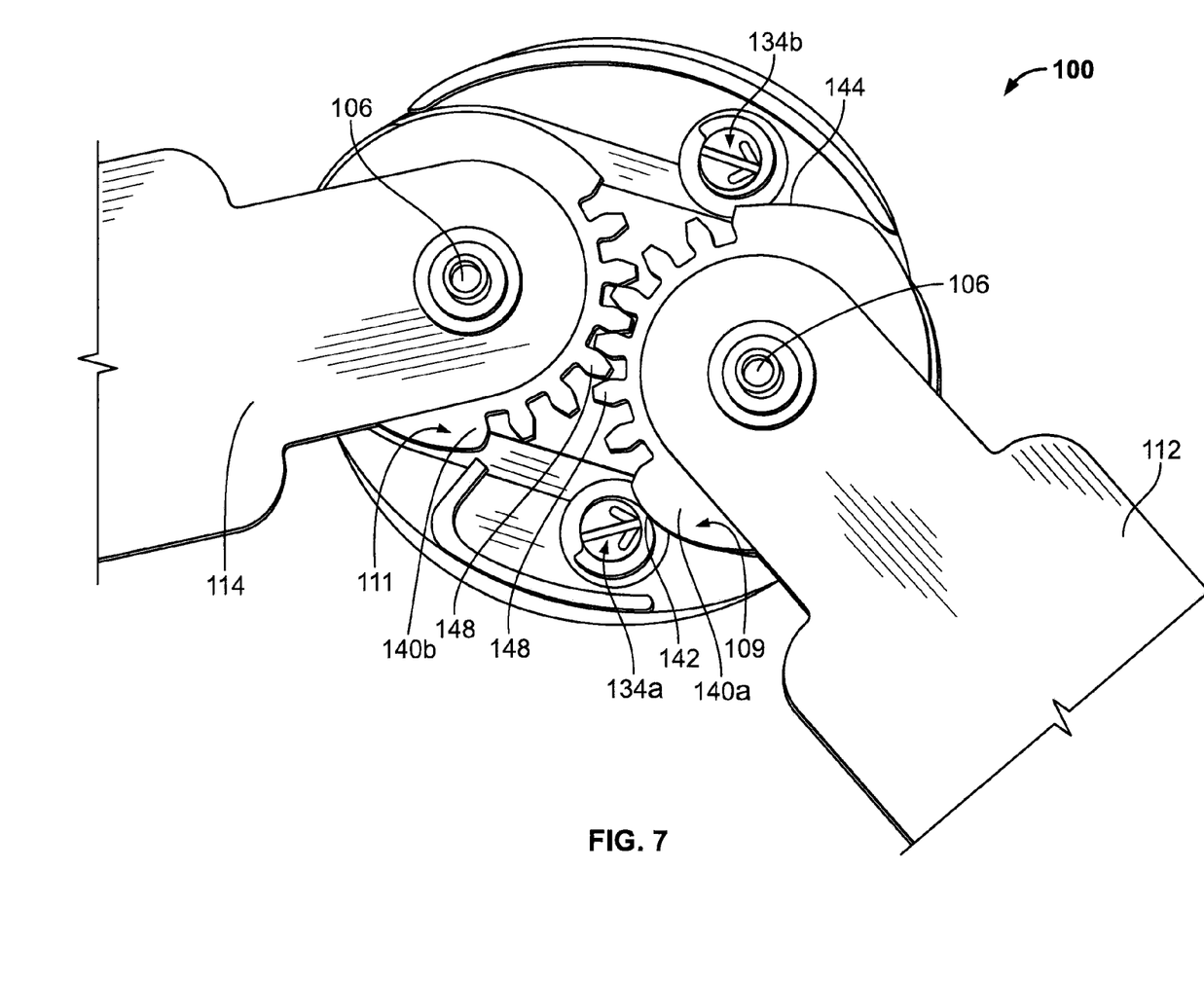
FIG. 7 is a perspective view of the adjustable hinge of FIG. 2A, shown with first and second brace arms in flexion.
Figure 8:
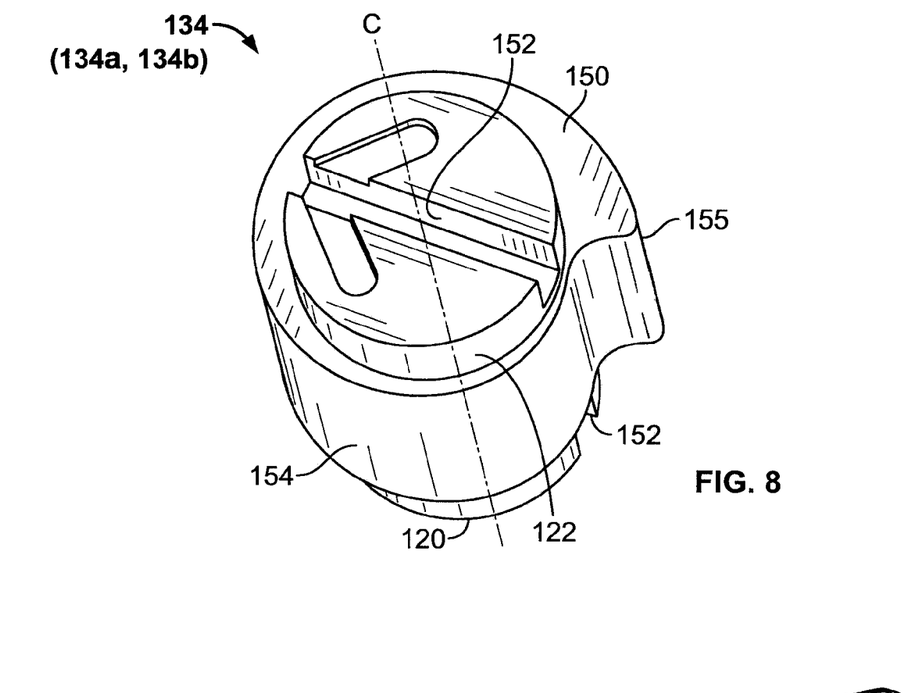
FIG. 8 is a perspective view of a control device of the adjustable hinge of FIG. 2A according to the present teachings.
Figure 9:
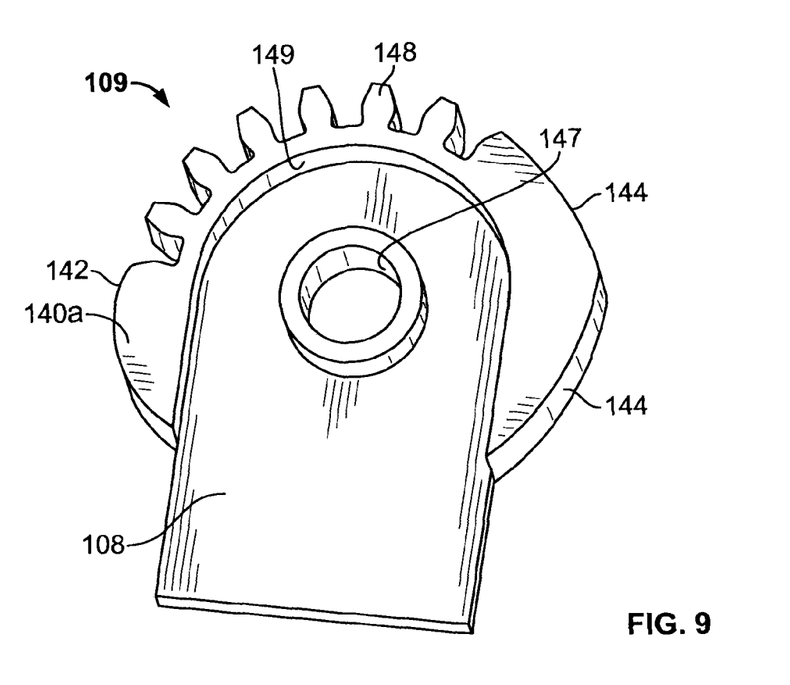
FIG. 9 is a perspective view of a first member of the adjustable hinge of FIG. 2A according to the present teachings.
Figure 10:
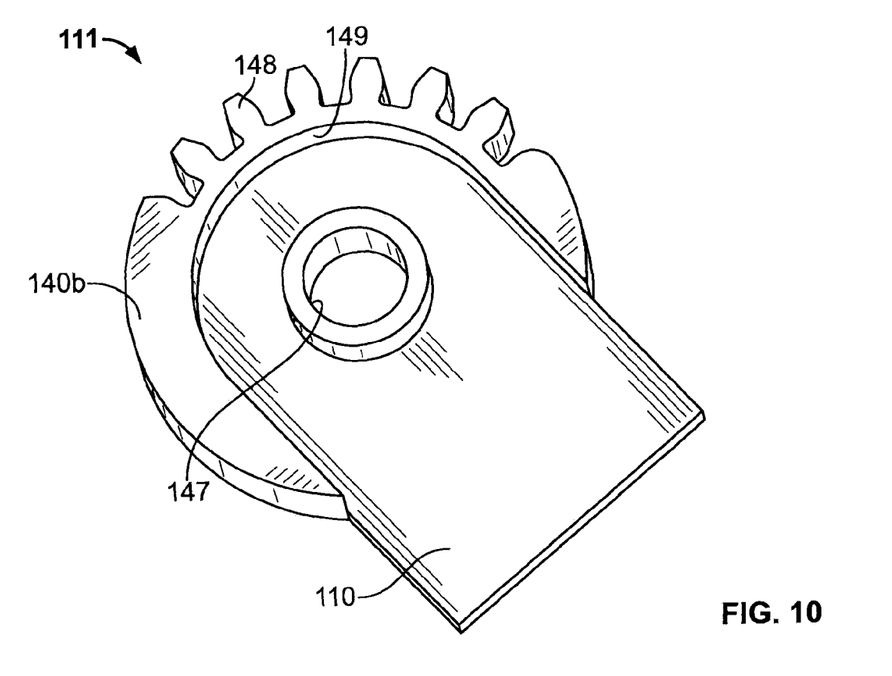
FIG. 10 is a perspective view of a second member of the adjustable hinge of FIG. 2A according to the present teachings.

Referring to FIGS. 8-10, the first and second members 109, 111 can include corresponding first and second gear portions 140a, 140b and first and second gear arms 108,110. Each of the first and second members 109, 111 can include a recess 149 surrounded by the corresponding gear portion 140a, 140b. Each of the first and second gear portions 140a, 140b can include a plurality of gear teeth 148 along an arcuate periphery thereof. Referring to FIGS. 4-6, the teeth 148 of the first and second members 109, 111 can be meshingly engaged for rotation about the first and second axes A, B that pass through the first and second pivot members 106. The first and second axes A, B can be perpendicular to the first and second gear portions 140a, 140b and to the front and back outer surfaces 102a, 104a of the housing 105. The recesses 149 of the first and second members 109, 111 can be shaped and sized to conform to distal ends of the corresponding brace arms 112, 114. It will be appreciated, however, that the brace arms 112, 114 can have various shapes and sizes and can be adjusted for attachment to any orthopedic brace 90, such as the orthopedic brace shown in FIG. 1. The brace arms 112, 114 can be attached to first and second members 109, 111 using the pivot members 106 and can rotate with the first and second members 109, 111 about the first and second axes A and B. The first and second brace arms 112, 114 can be radiolucent, and can be made from carbon, for example, or other lightweight materials.

Figure 8A:
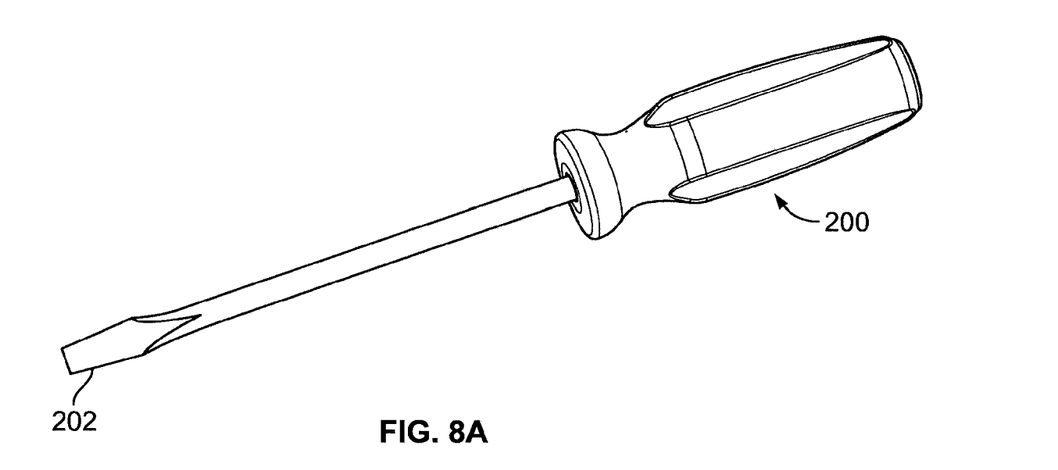
FIG. 8A is a perspective view of a driver tool for the control device of FIG. 8.

The first gear portion 140a of the first member 109 can include first and second cam surfaces 142, 144 for controlling a rotational range of motion in first and second opposing rotational directions, such as rotational directions corresponding to flexion and extension or overextension of the associated anatomic joint 80 in relation with corresponding first and second (or flexion and extension) control devices 134. The first and second control devices 134 are substantially identical and will also be referenced with characters 134a (flexion control device), 134b (extension control device) in reference to FIGS. 4-8. Referring to FIG. 8, each control device 134 can include a cylindrical surface 154 along a longitudinal axis C of the control device 134 and an asymmetric cam extension 150 defining a cam surface 155. Each control device 134 can also include upper and lower portions 120, 122 extending through corresponding openings of the housing 105. Each of the upper and lower portions 120, 122 can include a tool engagement formation 152, such as, for example, a slot for engaging a driver tool 200. An exemplary driver tool 200 in the form of a screwdriver having a driver engagement blade 202 is shown in FIG. 8A. The driver tool 200 can engage the tool engagement formation 152 and rotate each of the first and second control devices 134a, 134b about their longitudinal axis C by a selected angle, such that the cam extension 150 and the cam surface 155 of each control device 134a, 134b can be at a desired orientation relative to the corresponding first and second cam surfaces 142, 144 of the first member 109 for limiting the range of flexion and extension or overextension, as discussed below. Referring to FIG. 4, the first control device 134a can be placed adjacent the first cam surface 142 of the first member 109 and the second control device 134b can be placed adjacent the second cam surface 144 of the first member 109. It will be appreciated that the first and second members 109, 111 can be interchanged so that the first and second control devices 134a, 134b can be placed adjacent to opposite sides of the second member 109 at corresponding cam surfaces. Further, it is possible to place the first and second cam surfaces 142, 144 on different of the first and second members 109, 111 with corresponding positioning of the first and second control devices 134a, 134b.

Figure 3:
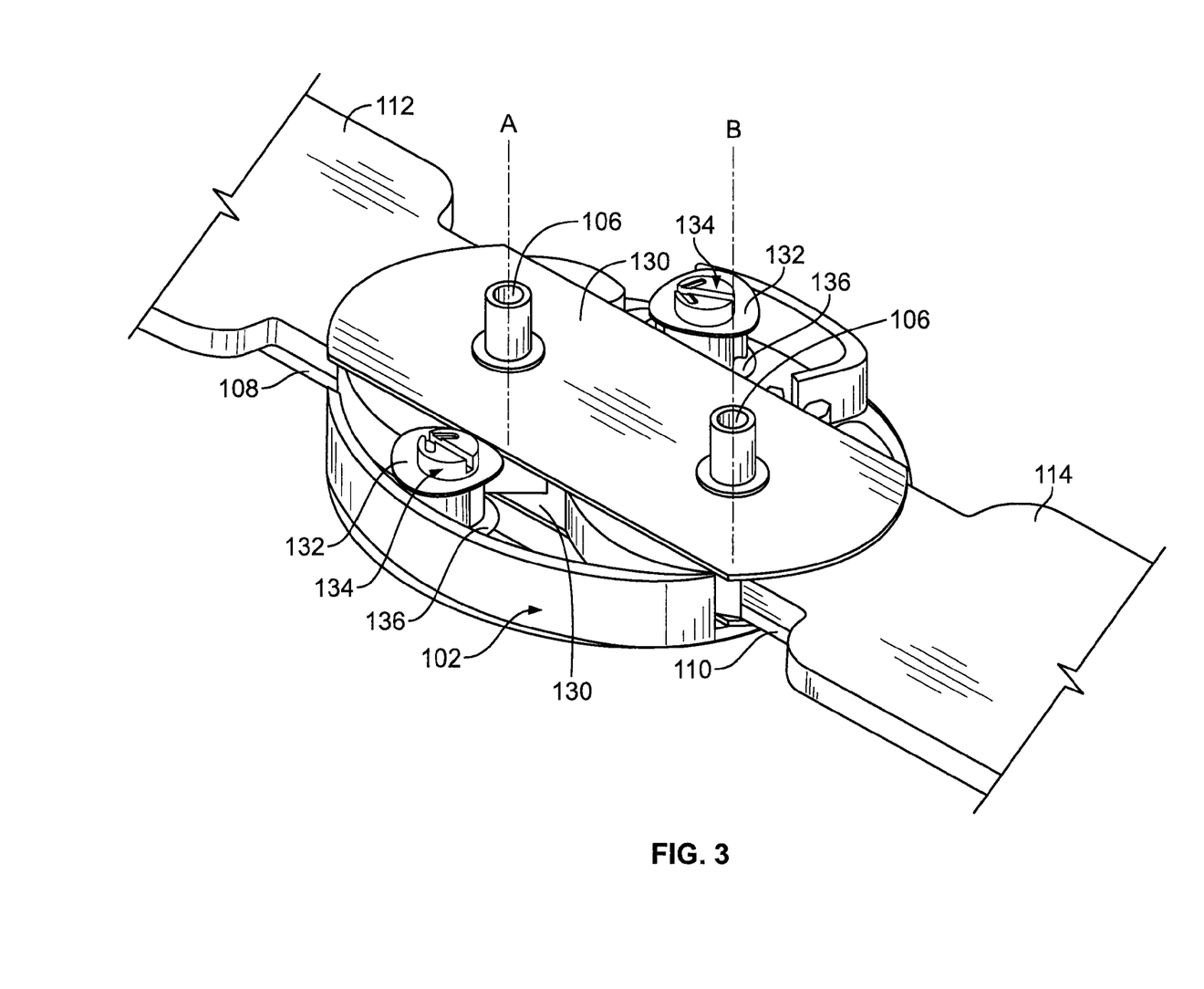
FIG. 3 is a perspective view of the adjustable hinge of FIG. 2A, shown with a back cover removed.

The first and second control devices 134 can be supported between the front and back covers 102, 104 of the housing 105 with the upper and lower portions 120, 122 accessible through the housing 105. Referring to FIGS. 3-6, each of the first and second control devices 134 can include a spring washer 132 on the side of the back cover 104 and a friction or lock washer 136 on the opposite side of the control device 134 adjacent the front cover 102. The spring washer 132 can be an annular leaf spring, and the friction washer 136 can be an anti-slip annular washer including serrations or other ridges for increasing frictional engagement with the inner surface of the housing 105. The friction washer 136 can prevent accidental rotation of the cam extension 150 of the control device 134. The spring washer 132 can provide a biasing force along the longitudinal axis C of the control device 134 for holding the control device 134 against the friction washer 136. The spring washer 132 can be, for example, metallic, and the friction washer 136 can be, for example, a rubber or carbon or other type of washer. Additionally, anti-wear protective washers 130 can be placed inside the front and back covers 102, 104 for protecting the first and second gear portions 140a, 140b from wear or abrasion, as shown in FIGS. 3 and 4, when the housing 105 and the first and second gear portions 109, 111 are made of metallic or other materials that can be abraded or wear out by repeated contact and motion.

Each of the first and second control devices 134a, 134b can be rotated with a driver tool 200 that engages the slot 152. The first control device 134a can be rotated such that the cam surface 155 of the cam extension 150 of the first control device 134a can contact the first cam surface 142 of the first member 109 at a selected degree of flexion between the first and second members 109, 111, and can prevent further flexion of the first and second brace arms 112, 114 and further flexion of the associated anatomic joint 80. Similarly, the second control device 134b can be rotated such that the cam surface 155 of the cam extension 150 of the second control device 134b can contact the second cam surface 144 of the first member 109 at a selected degree of extension between the first and second members 109, 111, and can prevent further extension of the first and second brace arms 112, 114 and corresponding extension or overextension of the associated anatomic joint 80, as discussed below.

Figure 2A:
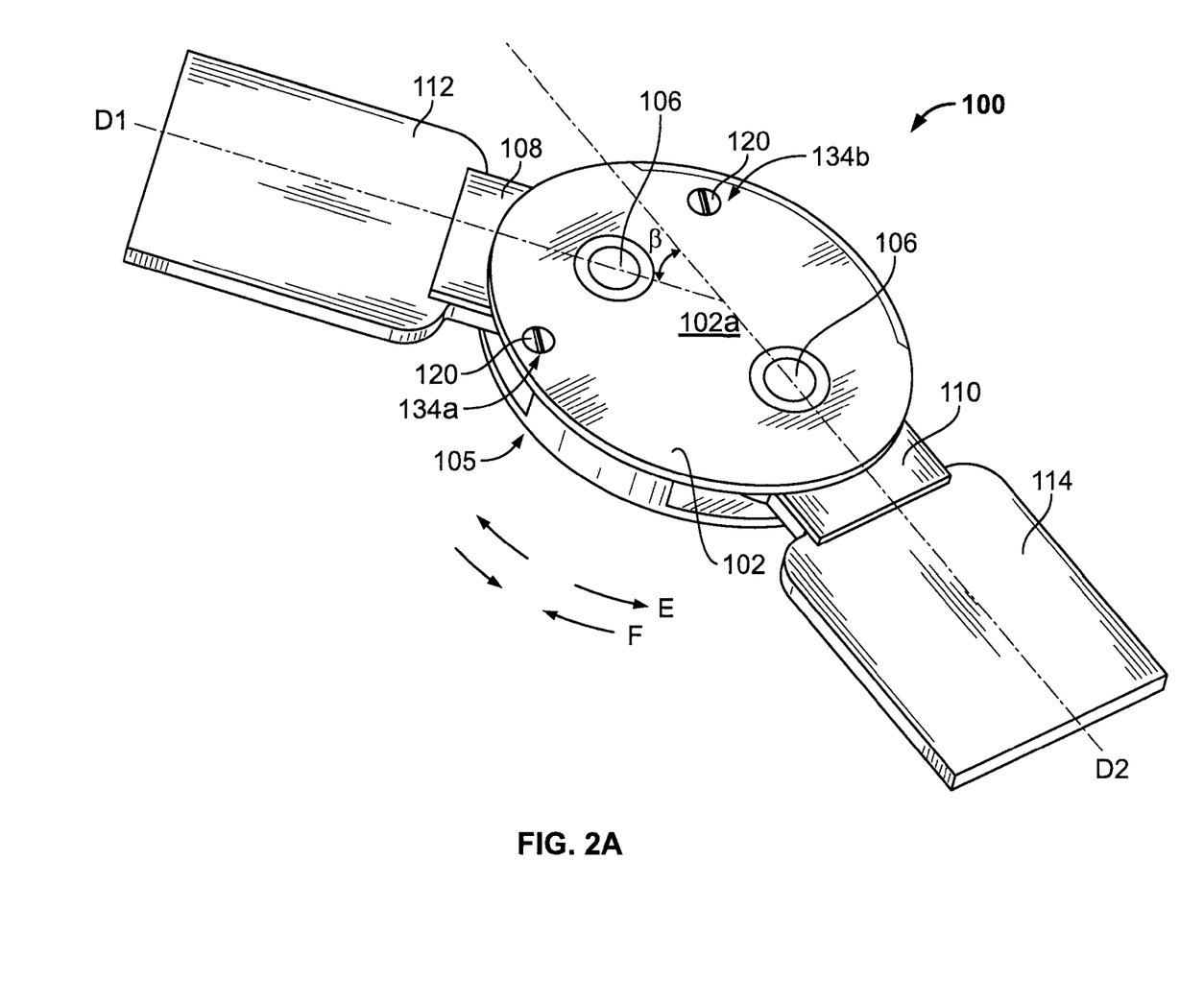
FIG. 2A is a perspective front view of an adjustable hinge according to the present teachings.
Figure 2B:
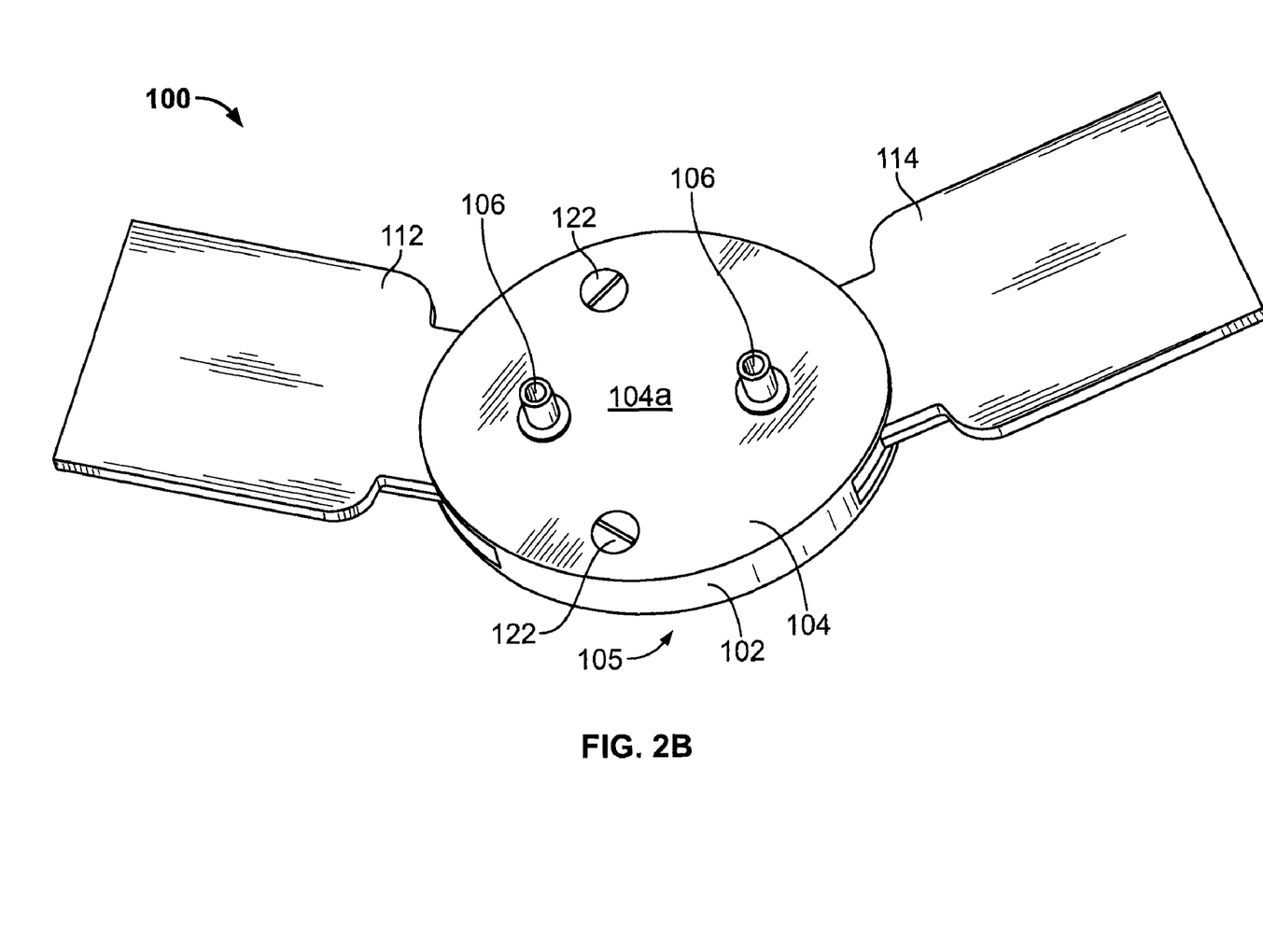
FIG. 2B is a perspective back view of the adjustable hinge of FIG. 2A.

Referring to FIG. 2A, the range of motion in flexion and extension can be defined in reference to first and second longitudinal axes D1, D2 associated with the first and second brace arms 112, 114 and to the corresponding first and second members 109, 111. An angle β between the first and second longitudinal axes D1, D2 of the brace arms 112, 114 can have a zero value for regular extension, a positive value for flexion, and a negative value for overextension. The first control device 134a can be adjusted to prevent flexion beyond a selected value of β, such as 120 degrees, for example. Similarly, the second control device 134b can be adjusted to prevent overextension beyond a selected value of β, such as minus 10 degrees, for example. It will be appreciated that flexion and extension/overextension correspond to first and second opposing rotations of the anatomic joint 80, and of the first and second members 109, 111 and the corresponding first and second gear portions 140, 140b, as shown in FIG. 2A by curved arrows F and E. The range of motion in flexion and extension for this example is defined from minus 10 degrees to 120 degrees. In general, the range of motion can be determined by limiting values $\beta_1$ and $\beta_2$, such that $\beta_1 \leq \beta \leq \beta_2$. The values for $\beta_1$ and $\beta_2$ can be selected by a healthcare professional for the particular patient. Further, the values for $\beta_1$ and $\beta_2$ can be varied by any desired degree in a continuous manner, by simply rotating the corresponding first and second control devices 134a, 134b by a corresponding degree. In other words, the rotational adjustment is continuous, thereby providing an infinite number of adjustability positions.

Referring to FIGS. 1, 2A, 2B, 8 and 8A, the adjustable hinge 100 can be used with an orthopedic brace 90 that can be positioned about an anatomic joint 80 between first and second anatomic members 82, 84, such as a femur and tibia associated with a knee joint. An exemplary knee brace 90 is illustrated in FIG. 1. The brace 90 can include first and second brace portions 92, 94 mountable on the first and second anatomic members 82, 84. The first brace portion 92 can be mounted on the first anatomic member 82 with one or more straps, such as straps 91, 93. Similarly, the second brace portions 94 can be mounted on the second anatomic member 884 with one or more straps, such as straps 95, 97. The first and second brace arms 112, 114 can be attached to the first and second brace portions 92, 94 such that the adjustable hinge 100 can be adjacent to the anatomic joint 80. A pad or other cushioning member 96 can be supported between the housing 105 of the adjustable hinge and the anatomic joint 80. The adjustable hinge 100 can be adjusted to control the range of motion of the anatomic joint in flexion and extension or overextension, as discussed above.

It will be appreciated that the adjustable hinge 100 can be provided in a compact form and can be adjusted without dismantling or removing it or opening the housing 105 with the use of a readily available tool, such as an ordinary screwdriver. In addition, the range of motion of the adjustable hinge 100 can be adjusted in a continuous manner by any desirable increment, by simply rotating one or both of the first and second control devices 134a, 134b by a desired degree of rotation.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above.

Further, it will recognized that geometric characterizations such as, for example, "parallel" and "perpendicular", are not made in reference to mathematical or absolute abstractions, but should be interpreted to allow small deviations or tolerances based on ordinary manufacturing standards, as understood by the person of ordinary skill in the art.

Moreover, many modifications may be made to adapt a particular situation or material to the teachings of the invention without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. A medical device comprising:
   an adjustable hinge for an orthopedic brace, the adjustable hinge including:
   a housing;
   a first member rotatably supported by the housing, the first member having a first gear portion pivotable about a first axis, the first gear portion having a first plurality of teeth and first and second cam surfaces;
   a second member rotatably supported by the housing, the second member having a second gear portion pivotable about a second axis, the second axis parallel and spaced apart from the first axis, the second gear portion having a second plurality of teeth engageable with the first plurality of teeth;
   a first control device rotatably supported on the housing, the first control device having a third cam surface, the third cam surface selectively rotatable in and out of engagement with the first cam surface and controlling a range of motion of the first and second gear portions in a first rotational direction; and
   a second control device rotatably supported on the housing, the second control device having a fourth cam surface, the fourth cam surface selectively rotatable in and out of engagement with the second cam surface and controlling a range of motion of the first and second gear portions in a second rotational direction opposite to the first rotational direction.

2. The medical device of claim 1, wherein the first and second members include corresponding first and second recesses receiving first and second brace arms couplable with the orthopedic brace, the first and second brace arms respectively pivotable about the first and second axes.

3. The medical device of claim 1, wherein the third and fourth cam surfaces are formed on corresponding first and second cam extensions of the first and second control devices.

4. The medical device of claim 3, wherein rotational positions of the first and second cam extensions determine a range of motion of the first and second gear portions respectively in flexion and extension/overextension.

5. The medical device of claim 3, wherein first and second control devices include first and second driver engagement formations for rotating the first and second cam extensions.

6. The medical device of claim 1, further comprising first and second spring washers surrounding the corresponding first and second control devices and biasing the first and second control devices axially against the housing.

7. A medical device comprising:
   an orthopedic brace for an anatomic joint;
   an adjustable hinge coupled to the brace and controlling a range of motion of the anatomic joint, the adjustable hinge including:
   first and second gear portions rotatable about first and second axes, the first and second axes parallel to and spaced apart from one another, the first and second axes perpendicular to the first and second gear portions, the first gear portion including a first cam surface; and
   a flexion control device having a flexion cam surface, the flexion control device selectively rotatable about a third axis parallel to the first and second axes, the flexion cam surface engaging the first cam surface of the first gear portion at a selected angle of flexion of the anatomic joint and preventing further flexion; and first and second brace arms connected to the orthopedic brace at opposite sides to the anatomic joint, the first and second brace arms coupled to and rotatable with the first and second gear portions.

8. The medical device of claim 7, further comprising an extension control device having an extension cam surface, the extension control device rotatable about a fourth axis parallel to the first and second axes, the extension cam surface engaging a second cam surface of the first gear portion at a selected angle of extension/overextension and preventing further extension.

9. The medical device of claim 8, further comprising a housing rotatably supporting the first and second gear portions, the flexion control device and the extension control device.

10. The medical device of claim 8, wherein each of the flexion control device and the extension control device includes a driver engagement formation extending through an outer surface of the housing.

11. The medical device of claim 7, wherein a portion of the first brace arm is received in a conforming recess of the first gear portion and is rotatable about the first axis, and wherein a portion of the second brace arm is received in a conforming recess of the second gear portion and is rotatable about the second axis.

12. The medical device of claim 7, further including a spring washer coupled to the flexion control device and biasing the flexion control device along the third axis.

13. The medical device of claim 12, further comprising a friction washer coupled to the flexion control device opposite the spring washer.

14. The medical device of claim 7, wherein the first gear portion includes a first plurality of teeth meshingly engaged with a second plurality of teeth of the second gear portion.

15. A method of controlling a range of motion of an anatomic joint, the method comprising:
   attaching a first brace portion to a first anatomic member of an anatomic joint;
   attaching a second brace portion to a second anatomic member of the anatomic joint;
   connecting the first brace portion to a first brace arm;
   connecting the second brace portion to a second brace arm;
   coupling the first brace arm to an adjustable hinge for rotation about a first pivot axis of the adjustable hinge;
   coupling the second brace arm to the adjustable hinge for rotation about a second pivot axis of the adjustable hinge, the second pivot axis parallel to the first pivot axis; and
   rotating a flexion control device of the adjustable hinge about a third pivot axis parallel to the first and second pivot axes by a first selected degree of rotation; and
   limiting a range of flexion between the first and second brace arms based on the selected degree of rotation.

16. The method of claim 15, further comprising:
   rotating an extension control device of the adjustable hinge about a fourth pivot axis parallel to the first and second pivot axes by a second selected degree of rotation; and
   limiting a range of extension between the first and second brace arms based on the second selected degree of rotation.

17. The method of claim 15, wherein limiting a range of flexion between the first and second brace arms based on the first selected degree of rotation includes engaging a first cam surface of the first gear portion with a cam surface of the flexion control device.

18. The method of claim 16, wherein limiting a range of extension between the first and second brace arms based on the second selected degree of rotation includes engaging a second cam surface of the first gear portion with a cam surface of the extension control device.

19. The method of claim 15, wherein rotating a flexion control device includes engaging a driver engagement formation of the flexion control device with a driver tool through an outer surface of a housing of the adjustable hinge.

20. The method of claim 16, wherein rotating an extension control device includes engaging a driver engagement formation of the extension control device with a driver tool through an outer surface of a housing of the adjustable hinge.

* * * * *